United States Patent
Liebmann-Vinson et al.

(10) Patent No.: US 7,198,855 B2
(45) Date of Patent: Apr. 3, 2007

(54) METHODS OF SURFACE MODIFICATION OF A FLEXIBLE SUBSTRATE TO ENHANCE CELL ADHESION

(75) Inventors: Andrea Liebmann-Vinson, Willow Springs, VA (US); Bryce Chaney, Durham, NC (US); Kirill Efimenko, Raleigh, NC (US); Jan Genzer, Raleigh, NC (US)

(73) Assignees: Becton, Dickinson and Company, Franklin Lakes, NJ (US); North Carolina State University, Raleigh, NC (US)

( * ) Notice: Subject to any disclaimer, the term of this patent is extended or adjusted under 35 U.S.C. 154(b) by 147 days.

(21) Appl. No.: 10/660,760

(22) Filed: Sep. 12, 2003

(65) Prior Publication Data

US 2005/0058842 A1   Mar. 17, 2005

(51) Int. Cl.
*B32B 27/06* (2006.01)
*B32B 27/18* (2006.01)
*B05D 3/12* (2006.01)

(52) U.S. Cl. ............ 428/447; 428/448; 427/2.1; 427/2.11; 427/2.31; 427/289

(58) Field of Classification Search ............ None
See application file for complete search history.

(56) References Cited

U.S. PATENT DOCUMENTS

| | | |
|---|---|---|
| 4,789,601 A | 12/1988 | Banes |
| 4,822,741 A | 4/1989 | Banes |
| 4,839,280 A | 6/1989 | Banes |
| 4,851,521 A | 7/1989 | della Valle et al. |
| 5,278,063 A | 1/1994 | Hubbell et al. |
| 5,567,598 A | 10/1996 | Stitt et al. |
| 5,998,517 A | 12/1999 | Gentle et al. |
| 6,037,141 A | 3/2000 | Banes |
| 6,048,723 A | 4/2000 | Banes |
| 6,057,150 A | 5/2000 | Lee et al. |
| 6,080,574 A | 6/2000 | Berndt |
| 6,107,083 A | 8/2000 | Collins et al. |
| 6,218,178 B1 | 4/2001 | Banes |
| 6,395,506 B1 | 5/2002 | Pitner et al. |
| 6,423,372 B1 * | 7/2002 | Genzer et al. ............ 427/250 |
| 6,649,403 B1 * | 11/2003 | McDevitt et al. ......... 435/288.5 |
| 6,680,206 B1 * | 1/2004 | McDevitt et al. .......... 436/172 |
| 6,692,914 B1 * | 2/2004 | Klaerner et al. ............ 435/6 |
| 6,713,298 B2 * | 3/2004 | McDevitt et al. ......... 435/287.8 |
| 6,770,323 B2 * | 8/2004 | Genzer et al. ............ 427/248.1 |
| 2002/0182633 A1 * | 12/2002 | Chen et al. ................ 435/7.1 |
| 2003/0035786 A1 * | 2/2003 | Hendriks et al. ......... 424/78.17 |
| 2003/0064422 A1 * | 4/2003 | McDevitt et al. .......... 435/7.32 |
| 2004/0053322 A1 * | 3/2004 | McDevitt et al. .......... 435/7.1 |
| 2006/0228256 A1 * | 10/2006 | McDevitt et al. ......... 422/82.05 |

OTHER PUBLICATIONS

Brandley et al., Anal. Biochem. (1988) 172:270.
Chaudury et al., Langmuir, (1991) 7:1013-1025.
Choi et al., Biomaterials (1999) 20:409-417.
Costello et al., Macromolecules (1987) 20:2819-2828.
Couchman et al., J.Cell Biol.,(1992) 93:402-410.
Efimenko et al., J. Colloid Interface Sci., (2002) 254(2):306-315.
Efimenko et al., Adv. Matl., (2001) 13:1560-63.
Genzer et al., Science (2000) 290:2130-33.
Grinnell, F., Int. Rev. Cytology (1978) 53:67-149.
Gutsche et al., Biomaterials (1996) 17:387-393.
Hern et al., J. Biomed. Mater. Res. (1998) 39:266-276.
Hsiue et al., J. Biomed. Mater. Res., (1998) 42:134-147.
Kim et al., Ann. Surgery (1998) 228:8-13.
Kleinman, et al., Biochem. Biophys. Res. Commun. (1976) 72:426-432.
Lateef et al., Biomaterials, (2002) 23: 3159-3168.
Lee et al., Journal of Polymer Science: Part A: Polymer Chemistry, (1996) 34:141-148.
Lu et al., Biomaterials (2000) 21: 1595-1605.
Madihally et al., Biomaterials. (1999) 20:1133-42..
Mooney et al., Biomaterials (1996) 17:1417-1422.
Murakami et al., J. Colloid & Interface Science (1998) 200:192-94.
Oxley et al. Biomaterials (1993) 14:1064-1072.
Pearlstein, E., Nature (1976) 262:497-500.
Pinilla et al., Meth. Molec. Biol., (1996) 66:171-179.
Ranucci et al., Tissue Engineering (1999) 5: 407-420.
Saad et al., J. Biomed. Res. (1996) 32:355-366.
Silver et al., Biomaterials, (1999) 20: 1533-1543.
Silver et al., Journal of Biomedical Materials Research (1995) 29:535-548.
Singer et al., J. Cell Biol. (1987) 104:573-584.
Torres et al., Biomaterials (2000) 21:1607-19.
Volger et al., Journal of Biomedical Materials Research (1987) 21:1197-1211.

(Continued)

*Primary Examiner*—Michael J. Feely
(74) *Attorney, Agent, or Firm*—Sughrue Mion, PLLC (57) ABSTRACT

The present invention provides methods of producing a surface with enhanced cell-adhesive properties comprising applying a stress to a polymeric matrix. The strained matrix is then modified by grafting a self-assembled monolayer onto the strained matrix, with the self-assembled monolayer comprising at least one exposed functional group. At least one cell-adhesive molecule can then be coupled to the at least one exposed functional group on the self-assembled monolayer to produce a surface with enhanced cell-adhesive properties.

35 Claims, 2 Drawing Sheets

OTHER PUBLICATIONS

Whang et al., Polymer (1995) 36:837-842.
Wu et al., Macromolecules (2001) 34:684-86.
Zhang et al., J. Biomed. Mater. Res. (1999) 45:285-293.
Al, Hua, et al., "Gelatin-Glutaraldehyde Cross-Linking on Silicone Rubber to Increase Endothelial Cell Adhesion and Growth", *In Vitro Cell. Dev. Biol.—Animal 38*, (Oct. 2002), 487—492.

Puleo, D. A., et al., "A technique to immobilize bioactive proteins, including bone morphogenetic protein-4 (BMP-4), on titanium alloy", *Biomaterials 23*, (2002),2079-2087.
Völcker, N., et al., "Functionalization of silicone rubber for the covalent immobilization of fibronectin", *Journal of Materials Science: Materials in Medicine, vol. 12, No. 2*, (Feb 2001), 111-119(9).

* cited by examiner

Figure 1. Results of ESCA analysis at each stage in the modification process

Figure 2

METHODS OF SURFACE MODIFICATION OF A FLEXIBLE SUBSTRATE TO ENHANCE CELL ADHESION

BACKGROUND OF THE INVENTION

1. Field of the Invention

The present invention provides methods of producing a surface with enhanced cell-adhesive properties comprising applying a stress to a polymeric matrix. The strained matrix is then modified by grafting a self-assembled monolayer onto the strained matrix, with the self-assembled monolayer comprising at least one exposed functional group. At least one cell-adhesive molecule can then be coupled to the at least one exposed functional group on the self-assembled monolayer to produce a surface with enhanced cell-adhesive properties.

2. Background of Invention

Cell and tissue culture in vitro has been routinely practiced in many areas of the biological and medical arts. However, many primary cells derived from human tissues are not capable of being supported for survival, proliferation, or differentiation in vitro using the conventional tissue culture techniques. This inability has limited the application of cell culture in areas such as cellular therapies and drug screening because of a gap between the in vivo state of the cells where they are organized into three-dimensional tissues that are constantly subjected to mechanical stresses and deformations and the in vitro state where the cells try to recapitulate the in vivo state on a static two-dimensional surface. Bioengineered tissue/scaffold constructs have emerged that are starting to bridge the gap, addressing the three-dimensional aspects of living tissues. The importance of mechanical stresses on growth and differentiation of cells in living tissues has also been recognized and accordingly led to the development of in vitro cell culture systems allowing stresses to be applied.

For example, Flexcell culture systems from Flexcell International Corporation are able to apply tensile, compressive or shear stresses to cultured cells. (See, for example, U.S. Pat. Nos. 4,789,601, 4,822,741, 4,839,280, 6,037,141, 6,048,723, and 6,218,178.) U.S. Pat. No. 6,057,150 discloses that the application of a biaxial strain to an elastic membrane that may be coated with extracellular matrix proteins and covered with cultured cells. U.S. Pat. No. 6,107,081 discloses another system in which a unidirectional cell stretching device comprising an elastic strip is coated with an extracellular matrix on which cells are cultured and stretched.

The central component of the above-mentioned cell culture systems that allows for the application of mechanical stresses is a flexible substrate that can be deformed easily and in a controlled manner, and which also supports cell adhesion and growth comparable to conventional cell culture substrates. Silicones, such as poly(dimethyl siloxane) (PDMS), are particularly suitable for this application because they are not only highly flexible but also provide optical clarity that allows microscopic observation of the cell cultures. However, PDMS surfaces do not support cell adhesion, and must to be modified before they can be used as cell culture substrates. Surface modification of silicone surfaces is complex and requires the introduction of functional groups that either by themselves allow for cell attachment or that are available for subsequent coupling of cell adhesion promoting ligands, for example, —$NH_2$ or —COOH groups.

Radio-frequency (RF-) plasma treatment can be used to introduce functional groups into the polymer surfaces. For example, an oxygen plasma treatment can be used to turn a polystyrene surface that will support only limited cell adhesion into a surface that will readily support cell attachment and growth. However, plasma treated surfaces gradually degrade over time because of the migration of the polar functional groups away from the surface into the polymer bulk. This effect is increased in PDMS because of the high chain mobility caused by the low glass transition temperature (below room temperature) of PDMS. Murakami et al., *Journal of Colloid and Interface Science* 200: 192(1998).

Several alternative derivatization methods to create silicone-based cell culture substrates are disclosed in U.S. Pat. Nos. 4,789,601 and 4,822,741. Exposure of cured or uncured silicone to a Bunsen burner flame leads to the incorporation of elemental carbon particles that were found to increase biocompatibility. Amination induced by HCl treatment followed by exposure to $NH_4OH$ or ammonia vapor was also found to increase the biocompatibility of that surface. Amination followed by peptidization (covalent coupling of a peptide to glutaraldehyde activated aminated surface) presents yet another way to improve the biocompatibility of silicone. In yet another method, amination is achieved by co-curing a polyorganosiloxane with a primary amine- or carboxyl-containing silane or siloxane.

A drawback of these conventional surface modification techniques of silicones for cell culture application is the limited density of functional groups that are imposed on the surface, thus leading to limited cell attachments.

Genzer et al. have previously reported a surface derivatization method called mechanically assembled monolayers (MAMs) on elastomeric silicon substrates rendering the surfaces either super-hydrophobic (Genzer et al., *Science*, 290: 2130 (2000)), covalently coupled with dense polymer brushes (Wu et al., *Macromolecules*, 34: 684 (2001)), or expressing a chemical gradient on the surface (Efimenko et al., *Advanced Materials*, 13: 1560 (2001)). However, it is not clear whether the elastomeric silicon substrates modified by this surface derivatization method is feasible for cell culture and cell growth. Thus, there is a need in the art for improved substrates and methods for culturing cells that support cell adhesion, growth and differentiation and that allow the application of mechanical stress to the cells.

SUMMARY OF INVENTION

The present invention provides methods of producing a surface with enhanced cell-adhesive properties comprising applying a stress to a polymeric matrix. The strained matrix is then modified by grafting a self-assembled monolayer onto the strained matrix, with the self-assembled monolayer comprising at least one exposed functional group. At least one cell-adhesive molecule can then be coupled to the at least one exposed functional group on the self-assembled monolayer to produce a surface with enhanced cell-adhesive properties.

The present invention also provides a cell culture device. In the cell culture device of the present invention, cells adhere to at least one cell-adhesive molecule that is coupled to a self-assembled monolayer.

DETAILED DESCRIPTION OF INVENTION

The present invention provides methods of producing a surface with enhanced cell-adhesive properties comprising applying a stress to a polymeric matrix. The strained matrix is then modified by grafting a self-assembled monolayer onto the strained matrix, with the self-assembled monolayer comprising at least one exposed functional groups. At least one cell-adhesive molecule can then be coupled to the at least one exposed functional group on the self-assembled monolayer to produce a surface with enhanced cell-adhesive properties.

The methods of the invention result in a surface suitable for cell culture with enhanced cell-adhesive properties. As used herein, "enhanced cell-adhesive properties" is a relative term that requires comparing the cell-adhesive properties of the surface of the flexible polymer matrix with the cell-adhesive properties of the surface of the polymer matrix after performing the methods of the invention described herein. A "cell-adhesive property" is a property of the surface and is used to indicate the ability of live cells, or a live cell, to adhere or attach to the surface and be able to, at a minimum, withstand gentle sheer forces, e.g., gentle shaking, or removal and/or addition of culture media, without detaching. Of course, a surface's cell-adhesive properties may be stronger such that the attached live cells or cell may be able withstand virtually any amount of sheer force without detaching. As used herein, a live cell is a cell that is metabolically active. A live cell need not actively grow or actively divide, provided the cell is metabolically active.

Thus, the methods of the current invention increase the ability of live cells to attach or remain attached to the surface of the polymer matrix after treatment. The increase in ability of the cells to adhere can be examined in a number of ways including, but not limited to, examining the number of adherent cells with increasing sheer forces and performing competition assays. The surface may possess cell-adhesive properties prior to performing the methods of the present invention, or the surface may not possess any cell-adhesive properties prior to the methods of the present invention.

The present invention also provides a device comprising a surface, with the surface comprising a flexible polymer matrix, a mechanically self-assembled monolayer, and at least one cell-adhesive molecule coupled to the mechanically self-assembled monolayer through functional groups on the self-assembled monolayer. The surface of the self-assembled monolayer can be intensely packed, in an adjustable manner, with the cell-adhesive molecule. Cell-adhesive molecules, such as extracellular matrix (ECM) components or growth factors, are coupled to the exposed functional groups on the self-assembled monolayer. These functional groups are either "native" to the self-assembled monolayer material or are "introduced." Such immobilized cell-adhesive molecules provide sites on the surface for cell attachment. At the same time, the underlying polymer is flexible and deformable and can be stretched or otherwise deformed and released to impart mechanical forces to adhering, growing cells. This environment can more closely mimic the cells' environment in vivo than other conventional two-dimensional tissue culture substrates such as "tissue culture" polystyrene.

The polymer matrix must be elastomeric, flexible, and deformable. Preferably, the matrix is characterized by a strain of up to about 200% in response to an effective stress, more preferably, by a strain of up to about 100% in response to an effective stress, and still more preferably, by a strain of between about 40% and about 80% in response to an effective stress. By strain is meant deformation, defined as $\Delta L/L_0$, where $\Delta L$ is the change in length and $L_0$ is the original length. Preferably, the polymer matrix is characterized in that it undergoes an elastic stress-strain response in which the polymer matrix returns to approximately its original length after application and cessation of the stress.

The flexible polymer matrix comprises polydimethyl siloxane (PDMS) or any other polyorganosiloxane. Polyorganosiloxanes are linear and cyclic compounds such as, but not limited to, dimethylvinylsilyl-terminated dimethylpolysiloxanes, trimethylsilyl-terminated (methylvinyl)(dimethyl)polysiloxane copolymers, dimethylvinylsilyl-terminated (methylvinyl)(dimethyl)polysiloxane copolymers and cyclic methylvinylpolysiloxanes.

Chemical sensor particles may be dispersed in the flexible polymer matrix, which particles imparts the chemical sensing capability to the composition. For example, chemical sensor particles may be oxygen sensor particles capable of responding to oxygen present in a solution contacting the flexible polymer matrix. The oxygen-sensing particles may have a luminescent compound that changes its luminescent property in response to oxygen. Examples of luminescent oxygen-sensing particles include, but are not limited to, any salt of tris-4,7-diphenyl-1,10-phenanthroline ruthenium (II), any salt of tris-2,2'-bipyridyl-ruthenium (II), any salt of tris-1,7-diphenyl-1,10 phenanthroline ruthenium (II), and 9,10-diphenyl anthracene. Luminescent particles can also include platinum (II) octaethyl porphyrin complexes, palladium (II) octaethyl porphyrin complexes, palladium-meso-tetra(4-carboxyphenyl) porphine, palladium-meso-tetra(4-carboxyphenyl) porphyrin dendrimer and palladium-meso-tetra(4-carboxyphenyl) tetrabenzoporphyrin dendrimer.

Examples of salts of tris-4,7-diphenyl-1,10-phenanthroline ruthenium (II) include, but are not limited to, tris-4,7-diphenyl-1,10-phenanthroline ruthenium (II) dichloride pentahydrate, tris-4,7-diphenyl-1,10-phenanthroline ruthenium (III) trichloride, tris-4,7-diphenyl-1,10-phenanthroline ruthenium (II) diperchlorate and tris-4,7-diphenyl-1,10-phenanthroline ruthenium hexafluorophosphate. An example of a salt of tris-2,2'-bipyridyl-ruthenium (II) includes, but is not limited to, tris-2,2'-bipyridyl-ruthenium (II) chloride hexahydrate. An example of a salt of tris-1,7-diphenyl-1,10 phenanthroline ruthenium (II) includes, but is not limited to, tris-1,7-diphenyl-1,10 phenanthroline ruthenium (II) dichloride.

The polymer matrix may be in the form of a three-dimensional scaffold having internal surfaces to which the self-assembled monolayer is grafted and the cell-adhesive molecule is subsequently coupled.

The methods of the current invention comprise grafting a self-assembled monolayer onto the surface of the strained polymeric matrix. The self-assembled monolayers used in the present invention are alkylsilane derivatives, which are represented by the formulae $RSiX_3$, $R_2SiX_2$, or $R_3SiX$, wherein X is chloride or alkoxy and R is a carbon chain containing the functional groups. The exposed functional groups of the self-assembled monolayer may be amines, thiols, pyridyl, carboxyl, vinyl, sulfydryl, or aldehyde groups. In one embodiment, the self-assembled monolayer is a chlorosilane-based oligomer or polymer including, but not limited to, a trichlorosilane-based oligomer or polymer.

The methods of the current invention also comprise activating the exposed functional groups on the self-assembled monolayer by treating the self-assembled monolayer with a carbodiimide, along with a stabilizing reagent. The carbodiimide may be ethyldimethylaminopropylcarbodiimide (EDC). The reactive intermediate ester stabilizing compound may be N-hydroxysuccinimide (NHS), hydroxysulfosuccinimide, or hydroxybenzotriazolohydrate. In one embodiment, the reactive intermediate ester stabilizing compound is sulfo-NHS.

Next, the methods of the current invention comprise coupling at least one cell-adhesive molecule to the activated reactive groups. The coupling to the reactive groups can be any form of bond that attaches the cell-adhesive molecule to the activated, exposed reactive groups, such as, for example, an ionic bond, a hydrogen bond, a metallic bond, a polar bond, and a covalent bond including, but not limited to, peptide bonds.

As used herein, a cell-adhesive molecule is a molecule that increases adhesiveness of cells either to other cells, e.g., cell-cell adhesion molecules (CAMs), or to substrates or surfaces, e.g., cell-substrate adhesion molecule. Cell-adhesive molecules can be any class of chemical, including, but not limited to, a protein, a protein fragment, a polypeptide, an oligopeptide, an amino acid, a proteoglycan, a glycoprotein, a lipoprotein, a carbohydrate, a disaccharide, a polysaccharide, a nucleic acid, an oligonucleotide, a polynucleotide, a small organic molecule, a small inorganic molecule, a synthetic polymer and a natural polymer. Typical examples of cell-adhesive molecules include, but are not limited to, the major classes of traditional cell adhesion molecules, such as integrins, selecting, cadherins and the immunoglobulin members, as well as growth factors, extracellular matrix molecules, receptors and antibodies, or functional (i.e., binding) fragments thereof.

The major classes of cell adhesion molecules include the integrins, selecting, cadherins and members of the immunoglobulin (Ig) superfamily. Each of the classes of cell adhesion molecules include several, well-known members that are widely recognized in the art. Additionally, new cell-adhesive molecules may be identified by one of several ways, including but not limited to, interactions with antibodies known to disrupt cell adhesion, immunoprecipitation, cloning of putative CAMs or SAMs from expression libraries, binding or competition assays, conjugation of the putative cell-adhesive molecule to microspheres, attachment assays, centrifugal-force assays and transfection experiments. Examples of known cell adhesion molecules include, but are not limited to, E-cadherin, P-cadherin, N-cadherin, B-cadherin R-cadherin, EP-cadherin, OB-cadherin, M-cadherin, cadherin-5, cadherin-12, protocadherin 43, desmocollin 1, desmoglein 1, $\alpha_1\beta_1$integrin, $\alpha_2\beta_1$integrin, $\alpha_3\beta_1$integrin, $\alpha_4\beta_1$integrin, $\alpha_5\beta_1$integrin, $\alpha_V\beta_1$integrin, $\alpha_L\beta_2$integrin, $\alpha_M\beta_2$integrin, $\alpha_V\beta_3$integrin, P-selection, E-selectin, intercellular adhesion molecule 1 (ICAM 1), ICAM 2, neural cell adhesion molecule (NCAM), platelet-endothelial cell adhesion molecule (PECAM), vascular adhesion molecule (VCAM), carcinoembryonic antigen and L1.

Examples of antibodies, or functional fragments thereof, that are cell-adhesive molecules include, but are not limited to, CD34, CD133 and CD38. Examples of suitable growth factors include, but are not limited to, basic fibroblast growth factor (bFGF) and vascular endothelial growth factor (VEGF).

Extracellular matrix (ECM) molecules include, but are not limited to, the two major classes of ECM molecules: glycosaminoglycans and fibrous proteins. Glycosaminoglycans are polysaccharide chains that are usually covalently linked to a protein or proteoglycan. The fibrous proteins include, but are not limited to, collagen types, I, II, III, IV, V and VI, elastin, laminin, vitronectin and fibronectin.

The amount of cell-adhesive molecule used in the coupling reaction will vary, depending on several factors, including, but not limited to, the concentration or density of exposed, activated reactive groups on the surface, the desired increase in adhesiveness of the resulting surface, the chemical and physical properties of the cell-adhesive molecule, and the conditions (e.g., temperature, pressure, time and pH) under which the methods of the current invention take place.

The methods of the current invention encompass using one or more cell-adhesive molecules. For example, more than one type of cell-adhesive molecule, e.g., collagen I and collagen IV, may be coupled to the reactive groups, or a single type of cell-adhesive molecule, e.g., collagen VI, can be coupled to the reactive groups.

The present invention provides not only the above polymer composition providing for cell attachment and growth surface, but also a flexible cell culture system or vessel using this surface that supports cell attachment and growth while also being amenable to the application of physical stretching and deformation forces to cells cultured thereon. Thus, the present invention provides a cell culture device comprising the composition of the present invention for cell attachment and cell culture. In the cell culture device, the composition of the present invention is in, associated with, or in the form of, a cell culture vessel.

The cell culture vessel may be a multiwell microplate having wells, each of which comprises the polymer matrix. The cell culture device is susceptible to deformation upon application of mechanical forces such that adherent cells cultured in said device are subjected to the mechanical forces applied to and through the polymer matrix. The present invention further provides a cell culture comprising cells adherent to the composition of the present invention in the cell culture device of the present invention in cell culture medium.

Three-dimensional structures, e.g., foams, made out of silicone, incorporating internal surfaces that are modified with biologically active ligands, either with or without ruthenium dye, that can be subjected to mechanical stresses and strains.

The methods of the present invention can be performed as follows:

Application of Stress.

A stress is applied to a flexible polymer matrix to be used in the present invention, preferably a PDMS or any other polyorganosiloxane, resulting in a strain that is maintained (e.g., by clamping the material in a mechanical vice). The level of stress, and thus resulting strain, may be adjusted so that the surface area of the flexible polymer matrix that is available for the attachment of the self-assembled monolayer is adjusted, to thereby control and adjust the density of grafted self-assembled monolayer on the surface.

Modification with Self-Assembled Monolayer.

The surface of the strained polymer matrix is modified by grafting thereto a self-assembled monolayer having exposed functional groups, thereby producing a self-assembled monolayer-modified strained matrix. The self-assembled monolayer may have native exposed functional groups. Alternatively, the self-assembled monolayer may be chemically modified to introduce exposed functional groups prior to the addition of the cell-adhesive molecule.

When a flexible polymer matrix grafted with a self-assembled monolayer that has exposed functional groups has been provided the application of stress and modification with the self-assembled monolayer are omitted and the matrix is then modified with cell-adhesive molecule.

Coupling of the Cell-Adhesive Molecule.

The functional groups of the self-assembled monolayer may be activated by treating the self-assembled monolayer with a carbodiimide and a reactive intermediate ester stabilizing compound to form a stabilized active ester intermediate on the self-assembled monolayer. Then, a cell-adhesive molecule having free amine groups is added to the active ester intermediate resulting in the formation of amide bonds where the amine groups of the CAP bond covalently with the activated ester groups, thereby producing the composition.

The carbodiimide may be ethyldimethylaminopropylcarbodiimide (EDC). The reactive intermediate ester stabilizing compound may be N-hydroxysuccinimide (NHS), hydroxysulfosuccinimide, or hydroxybenzotriazolohydrate. Preferably, the reactive intermediate ester stabilizing compound is sulfo-NHS. The concentration of each of the EDC and the sulfo-NHS is between about 0.4 mg/ml and about 40 mg/ml, preferably between about 1 mg/ml and about 10 mg/ml; more preferably, the concentration of EDC and the sulfo-NHS are each about 4 mg/ml.

In another embodiment, a self-assembled monolayer may be provided with a functional group that is capable of reacting with a cell-adhesive molecule and result in coupling of the cell-adhesive molecule without prior activation. For example, coupling of amine-group containing cell-adhesive molecules to a self-assembled monolayer bearing aldehyde functional groups will occur spontaneously upon exposure of the aldehyde-terminated self-assembled monolayer with the cell-adhesive molecule-containing solution. In this example, a reducing agent may also be present in the cell-adhesive molecule solution to reduce the hydrolytically instable Schiff's bases that are formed between the aldehyde on the self-assembled monolayer and the amine on the cell-adhesive molecule to a more stable amide bond.

Release of Stress.

Finally, the stress applied on the flexible polymer matrix is released. The release occurs either after the self-assembled monolayer becomes grafted on the surface, but prior to the addition of the cell-adhesive molecule, or the polymer is maintained as a strained matrix and not released until the cell-adhesive molecule has been coupled to the functional groups of the self-assembled monolayer. In either case, the release of the flexible polymer causes the flexible polymer to return to its less stretched state, and the self-assembled monolayer and subsequently bonded cell-adhesive molecule become more condensely packed on the surface of the polymer matrix.

In the present invention, the density of the grafted self-assembled monolayers may be adjusted by the stretch extension of the polymer matrix, the degree of plasma treatment of the polymer matrix surface (which affects the number of graft points available on the surface), or the concentration of the self-assembled monolayer used in the grafting reaction. Further, the density of the cell-adhesive molecules may be adjusted by modifying the density of the self-assembled monolayer or adjusting the concentration of cell-adhesive molecules used in the coupling reaction or both methods.

Furthermore, the present invention provides a method for culturing cells on the devices of the present invention. Cells are added onto the device and permitted to adhere to the surface and grow in a culture medium. The cells cultured on the devices of the present invention may be subjected to a mechanical force by applying a stress to the polymer matrix that deforms the matrix. The stress to the polymer matrix is applied by methods known to those skilled in the art, for example, mechanical stretching or compression, shear force, or vacuum. Cells are grown on a substrate that comprises the above surface under conditions in which the cells are subjected to stresses and forces that can be imposed in a controlled manner.

On these flexible substrates, a mechanical force can be applied that is either constant or oscillatory. If the force is constant, it can be applied gradually so that the cell culture substrate is continuously expanding, thus, for example, preventing cell contact-contact growth inhibition. If the force is oscillatory, it may be applied in sinusoidal or any other wave form, as a step function, as a tensile force or a compressive force, by flexing and extending the material in one direction (unilaterally) or in different directions simultaneously (multilateral).

In this way, cell culture on this novel substrate can better mimic the environment in vivo. Therefore, this invention is particularly useful for ex vivo cell cultures that maintain primary cells explanted from a subject in a more physiologic state while permitting the study of the effects of various factors, such as drugs, on the cell morphology and function.

The following examples are illustrative, but not limiting the scope of the present invention. Reasonable variations, such as those that will be evident to the ordinary artisan, can be made herein without departing from the scope of the present invention.

EXAMPLES

Example 1

Preparation of a Silicone Surface by Applying Stress to the Polymer

PDMS networks were prepared by casting a mixture of PDMS (molecular weight=49.5 kDa) and a cross-linker into a film (thickness≈0.5 mm) and curing it at 55° C. for 1 hr under a vacuum. Following extraction in toluene (24 hrs), the samples were dried completely. Strips (1×5 cm) of the material were uniaxially stretched in a custom-designed apparatus and exposed to the UV/ozone treatment for 30 minutes, which produced PDMS-UVO surfaces with a large number of hydrophilic groups. The PDMS-UVO specimens were exposed to a vapor of undecenyl trichlorosilane (UTS), whose molecules formed a self-assembled monolayer (SAM) on the PDMS-UVO surfaces. After the UTS attachment, the strain was released from the substrate, which returned to its original size, causing the attached molecules to pack closely. The degree of packing of the UTS moieties was found to be proportional to the initial strain on the PDMS network. Carboxylic acid groups were generated on the surfaces by oxidizing the vinyl groups of UTS with $KMnO_4$. Finally, standard aqueous carbodiimide coupling chemistry (EDC/Sulpho-NHS) was used to covalently attach a biologically active ligand, e.g., the well-know cell-adhesive peptide GRGDS, to the carboxylic acids via a zero-length amide linkage.

Figure 1:
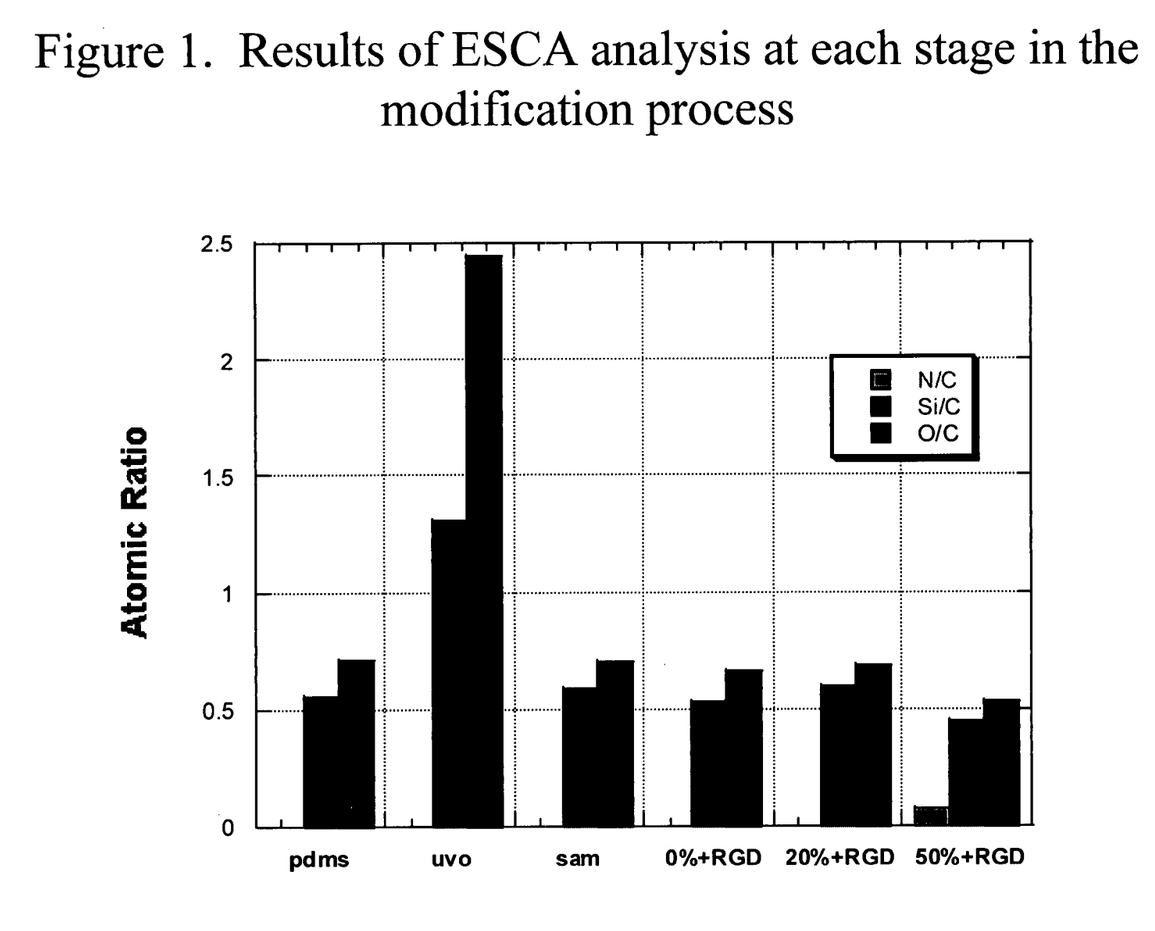
FIG. 1 depicts results from ESCA (Electron Spectroscopy for Chemical Analysis) at each stage in the modification process. Immobilized GRGDS peptide was identified on the PDMS substrate stretched 50% prior to UVO treatment (as evidence by the presence of nitrogen). This data indicates that increasing the strain applied to the sample also increases the grafting density of the ligand.

ESCA was used to confirm successful immobilization of the biologically active ligands by monitoring the atomic composition of the MAM surface, in particular nitrogen content, as shown in FIG. 1 and Table 1. Specifically, FIG. 1 shows that immobilized GRGDS was identified on the PDMS substrate stretched 50% prior to UVO treatment (as evidence by the presence of nitrogen). No nitrogen was detected on any sample prior to GRGDS coupling. Even after coupling, nitrogen was only detected for the 50% stretched sample, illustrating that the density of immobilized GRGDS was not sufficient to be detected by ESCA for samples stretched less than 50%. This data indicates that increasing the strain applied to the sample also increases the grafting density of the ligand.

Figure 2:
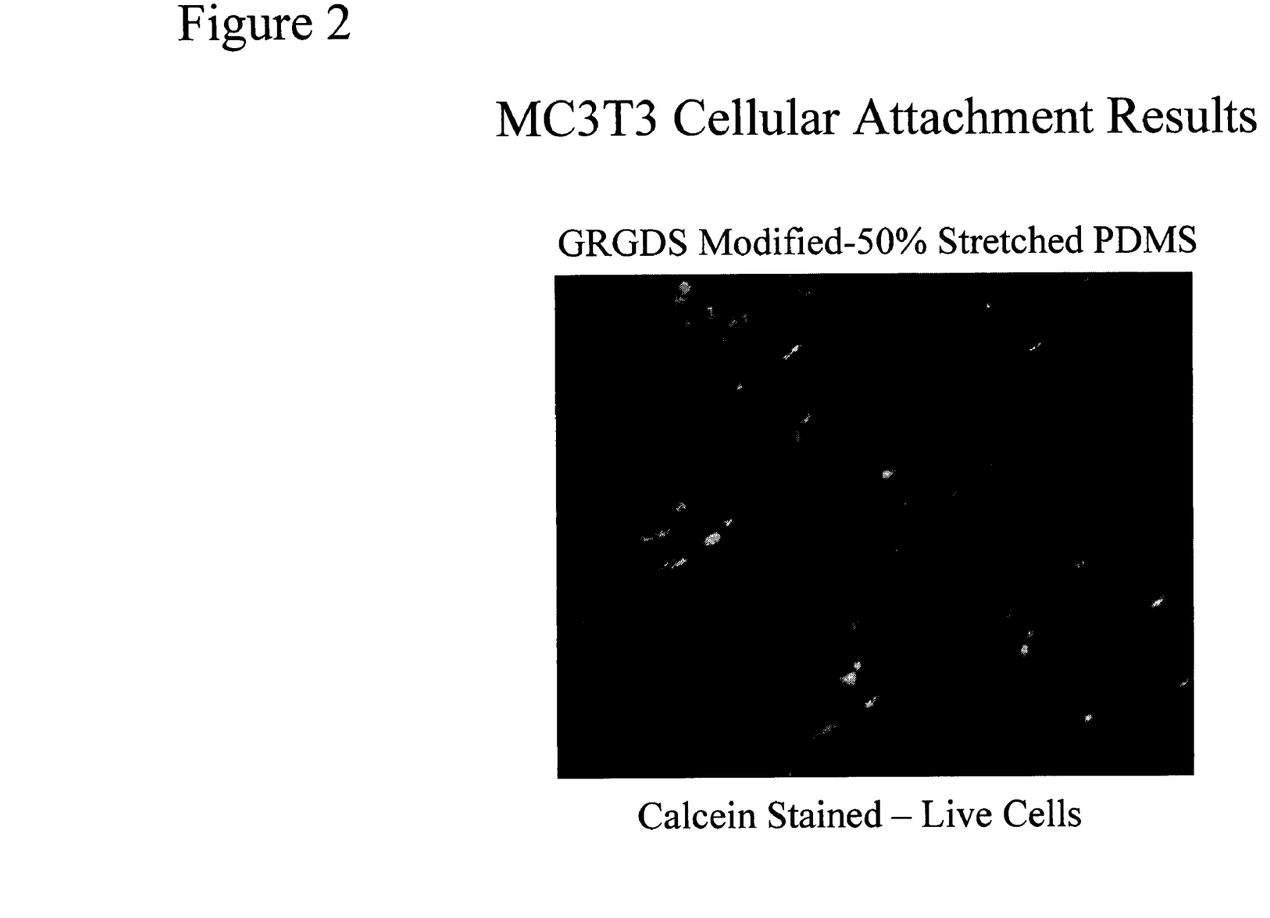
FIG. 2 depicts a micrograph of calcein-stained cells cultured on a surface prepared by the methods of the present invention.

MC3T3 cells were used to assess the bioactivity of grafted ligands. MC3T3 cells were cultured on GRGDS and fibronectin modified PDMS substrates in a low serum-containing medium (alpha-Modified Eagle Medium (Dubelco) with 2% fetal calf serum, 1% penicillin/streptomycin). Typically, MC3T3 cells are grown in 10% FCS containing media; however, to properly assess the bioactivity of the grafted GRGDS or fibronectin, lower serum concentrations were used as to not mask the biological effect of the GRGDS or fibronectin coupled to the surface. Cells adhered to both GRGDS modified and fibronectin modified substrates. See FIG. 2.

TABLE 1

Percentage of Elements Found at Various Levels of Surface Strain

| Sample Name | Elements Detected (in %) | | | | | | |
|---|---|---|---|---|---|---|---|
| | C | O | N | Si | O/C | N/C | Si/C |
| PDMS-No Treatment Control | 44.07 | 31.26 | ND | 24.67 | 0.71 | | 0.56 |
| UVO Treated Control | 21.05 | 51.28 | ND | 27.67 | 2.44 | | 1.31 |
| PDMS-UVO-SAM-Control | 43.69 | 30.44 | ND | 25.87 | 0.70 | | 0.59 |
| Sample A-0% Stretched + GRGDS | 45.64 | 30.19 | ND | 24.17 | 0.66 | | 0.53 |
| Sample B-20% Stretched + GRGDS | 43.81 | 30.04 | ND | 26.15 | 0.69 | | 0.60 |
| Sample C-50% Stretched + GRGDS | 49.35 | 26.30 | 2.38 | 21.97 | 0.53 | 0.05 | 0.45 |

What is claimed is:

1. A method for producing a surface with enhanced cell-adhesive properties, comprising:
   a. applying a stress to a flexible polymeric matrix wherein said polymeric matrix comprises chemical sensor particles dispersed in said matrix, said particles conferring chemical sensing capability;
   b. maintaining said flexible polymeric matrix as a strained matrix;
   c. modifying the surface of said strained matrix by grafting a self-assembled monolayer onto said strained matrix, said self-assembled monolayer comprising at least one exposed functional group;
   d. activating said at least one functional group of said self-assembled monolayer; and
   e. coupling at least one cell-adhesive molecule to said at least one activated functional group on said self-assembled monolayer.

2. The method of claim 1, wherein said strained flexible polymer matrix is released after said self-assembled monolayer becomes grafted on the surface and prior to the addition of said at least one cell-adhesive molecule.

3. The method of claim 1, wherein said strained flexible polymer matrix is maintained as a strained matrix until said at least one cell-adhesive molecule has been coupled to said at least one active functional group of said self-assembled monolayer.

4. The method of claim 1, wherein said self-assembled monolayer comprises an alkylsilane derivative represented by $RSiX_3$, $R_2SiX_2$, or $R_3SiX$, wherein X is chloride or alkoxy, and R is a carbon chain having said at least one functional group.

5. The method of claim 1, wherein said at least one functional group of said self-assembled monolayer are selected from amines, thiols, pyridyl, carboxyl, vinyl, sulfydryl, and aldehyde groups.

6. The method of claim 1, wherein said self-assembled monolayer has native exposed functional groups.

7. The method of claim 1, wherein said self-assembled monolayer has been chemically modified to have exposed functional groups.

8. The method of claim 1, wherein said activating said at least one functional group of said self-assembled monolayer comprises treating said self-assembled monolayer with a carbodiimide and a stabilizing compound to form at least one stabilized activated functional group on said self-assembled monolayer.

9. The method of claim 8, wherein said carbodiimide is ethyldimethylaminopropyl-carbodiimide (EDC).

10. The method of claim 8, wherein said stabilizing compound is selected from the group consisting of N-hydroxysuccinimide (NHS), hydroxysulfosuccinimide, and hydroxybenzotriazolohydrate.

11. The method of claim 10, wherein said stabilizing compound is sulfo-NHS.

12. The method of claim 10 wherein the concentration of each of said EDC and said sulfo-NHS are between about 0.5 mg/ml and about 10 mg/ml.

13. The method of claim 12, wherein said concentrations of said EDC and said sulfo-NUS are each about 4 mg/ml.

14. The method of claim 1, further comprising adjusting the density of said self-assembled monolayer to control the density of said at least one cell-adhesive molecule.

15. The method of claim 1, further comprising adjusting the density of said at least one functional group on said self-assembled monolayer to control the density of subsequently bonded at least one cell-adhesive molecule.

16. A device comprising a surface, said surface comprising
   a. a flexible polymer matrix, wherein said matrix comprises chemical sensor particles dispersed in said matrix, said particles conferring chemical sensing capability;
   b. a mechanically self-assembled monolayer; and
   c. at least one cell-adhesive molecule coupled to said mechanically self-assembled monolayer through at least one functional group on said self-assembled monolayer.

17. The device of claim 16, wherein said chemical sensor particles are oxygen sensor particles, capable of responding to oxygen present in a solution contacting the flexible polymer matrix.

18. The device of claim 16, wherein said flexible polymer matrix comprises a polyorganosiloxane.

19. The device of claim 18, wherein said polyorganosiloxane is polydimethyl siloxane (PDMS).

20. The device of claim 16, wherein said self-assembled monolayer is an alkylsilane derivative represented by $RSiX_3$, $R_2SiX_2$, or $R_3SiX$, wherein X is chloride or alkoxy, and R is a carbon chain comprising said at least one functional group.

21. The device of claim 16, wherein said at least one functional group of the self-assembled monolayer are amines, thiols, pyridyl, carboxyl, vinyl, sulfydryl, or aldehyde groups.

22. The device of claim 21, wherein said self-assembled monolayer is a chlorosilane-based oligomer or polymer.

23. The device of claim 22, wherein said self-assembled monolayer is a trichiorosilane-based oligomer or polymer.

24. The device of claim 16, wherein said cell-adhesive molecule comprises one or more peptides or polypeptides.

25. The device of claim 24, wherein said one or more polypeptides is an extracellular matrix (ECM) molecule.

26. The device of claim 25, wherein said ECM molecule is laminin.

27. The device of claim 25, wherein said ECM molecule is fibronectin.

28. The device of claim 24, wherein said one or more polypeptides is an antibody or antigen-binding fragment thereof.

29. The device of claim 24, wherein said one or more polypeptides is a growth factor.

30. The device of claim 16, wherein said polymer matrix is in the form of a three-dimensional scaffold having internal surfaces to which the self-assembled monolayer is grafted and the cell-adhesive molecule is bonded.

31. The device of claim 16, wherein said polymer matrix is characterized by a strain of up to about 200% in response to an effective stress.

32. The device of claim 16, wherein said polymer matrix is characterized by a strain of up to about 100% in response to an effective stress.

33. The device of claim 32, wherein said polymer matrix is characterized by a strain of between about 40% and about 80% in response to an effective stress.

34. The device of claim 32, wherein said polymer matrix is characterized in that it undergoes an elastic stress-strain response in which the polymer matrix returns to approximately its original length after application and cessation of the stress.

35. The device of claim 16, which is susceptible to deformation upon application of mechanical forces such that adherent cells cultured in said device are subjected to the mechanical forces applied to and through the polymer matrix.

* * * * *

UNITED STATES PATENT AND TRADEMARK OFFICE
CERTIFICATE OF CORRECTION

PATENT NO. : 7,198,855 B2 Page 1 of 1
APPLICATION NO. : 10/660760
DATED : April 3, 2007
INVENTOR(S) : Andrea Leibermann-Vinson et al.

It is certified that error appears in the above-identified patent and that said Letters Patent is hereby corrected as shown below:

Col. 10 at line 2 of claim 13, delete "sulfo-NUS" and insert thereof --sulfo-NHS--

Col. 10 at line 2 of claim 23, delete "trichiorosilane-based" and insert thereof --trichlorosilane-based--

Signed and Sealed this

Fifth Day of June, 2007

JON W. DUDAS
*Director of the United States Patent and Trademark Office*